(12) United States Patent
Murakami

(10) Patent No.: US 11,450,436 B2
(45) Date of Patent: Sep. 20, 2022

(54) METHOD AND APPARATUS FOR MACHINE LEARNING

(71) Applicant: FUJITSU LIMITED, Kawasaki (JP)

(72) Inventor: Katsuhiko Murakami, Yokohama (JP)

(73) Assignee: FUJITSU LIMITED, Kawasaki (JP)

( * ) Notice: Subject to any disclaimer, the term of this patent is extended or adjusted under 35 U.S.C. 154(b) by 312 days.

(21) Appl. No.: 16/875,036

(22) Filed: May 15, 2020

(65) Prior Publication Data

US 2020/0373012 A1  Nov. 26, 2020

(30) Foreign Application Priority Data

May 22, 2019  (JP) .............................. JP2019-096003

(51) Int. Cl.
  *G06K 9/00*   (2022.01)
  *G16H 50/20*  (2018.01)
  *G06K 9/62*   (2022.01)
  *G06N 20/00*  (2019.01)

(52) U.S. Cl.
  CPC .......... *G16H 50/20* (2018.01); *G06K 9/6218* (2013.01); *G06K 9/6267* (2013.01); *G06N 20/00* (2019.01)

(58) Field of Classification Search
  None
  See application file for complete search history.

(56) References Cited

U.S. PATENT DOCUMENTS

| 2010/0014455 A1 | 1/2010 | Oulai et al. |
| 2010/0144554 A1 | 6/2010 | Semizarov et al. |
| 2019/0026648 A1* | 1/2019 | Da .................... G06N 7/005 |

FOREIGN PATENT DOCUMENTS

| JP | 2012-507800 A | 3/2012 |
| WO | 2010/051320 A2 | 5/2010 |

OTHER PUBLICATIONS

Qi Shen et al., "contamDE: differential expression analysis of RNA-seq data for contaminated tumor samples", Bioinformatics, vol. 32(5), 2016, pp. 705-712, Advance Access Publication Date: Nov. 9, 2015 (Total 8 pages).

* cited by examiner

*Primary Examiner* — Soo Jin Park

(74) *Attorney, Agent, or Firm* — Fujitsu Patent Center

(57) ABSTRACT

Samples each including a feature amount and a label indicating one of a first value and a second value are classified into three or more clusters according to their feature amounts. Some of the clusters are combined to form a combined cluster on the basis of information on the number of samples with labels of the first value. The accuracy level of each sample with respect to the first value or the second value is calculated on the basis of the result of classifying into the combined cluster and the remaining clusters. Then, machine learning is performed using samples whose accuracy levels do not meet a prescribed condition more preferentially than samples whose accuracy levels meet the prescribed condition.

10 Claims, 9 Drawing Sheets

SAMPLE TABLE 126

| SAMPLE ID | GENE 1 | GENE 2 | ... | GENE m | LABEL |
|---|---|---|---|---|---|
| 1 | $x_{1,1}$ | $x_{1,2}$ | ... | $x_{1,m}$ | 0 (normal) |
| 2 | $x_{2,1}$ | $x_{2,2}$ | ... | $x_{2,m}$ | 0 (normal) |
| ... | ... | ... | ... | ... | ... |
| p | $x_{p,1}$ | $x_{p,2}$ | ... | $x_{p,m}$ | 0 (normal) |
| p+1 | $x_{p+1,1}$ | $x_{p+1,2}$ | ... | $x_{p+1,m}$ | 1 (cancer) |
| p+2 | $x_{p+2,1}$ | $x_{p+2,2}$ | ... | $x_{p+2,m}$ | 1 (cancer) |
| ... | ... | ... | ... | ... | ... |
| p+c | $x_{p+c,1}$ | $x_{p+c,2}$ | ... | $x_{p+c,m}$ | 1 (cancer) |

FIG. 4

METHOD AND APPARATUS FOR MACHINE LEARNING

CROSS-REFERENCE TO RELATED APPLICATION

This application is based upon and claims the benefit of priority of the prior Japanese Patent Application No. 2019-096003, filed on May 22, 2019, the entire contents of which are incorporated herein by reference.

FIELD

The embodiments discussed herein relate to a method and apparatus for machine learning.

BACKGROUND

Machine learning may be used for computer-based data analysis. In the machine learning, data indicating a plurality of samples with known results is entered into a computer. The computer then analyzes the data to generate a model that generalizes the correlation between cause (called "explanatory variable" or "independent variable") and result (called "response variable" or "dependent variable"). After that, the computer predicts results of unknown cases using the generated model.

Biomarker discovery is an application example of machine learning. A biomarker is a feature of a biological material such as a protein or a gene and serves as an indicator having a correlation with the presence or absence of a particular disease or the progress of the disease. Biomarkers may be used for diagnosis of a particular disease and confirmation of therapeutic effects. In the biomarker discovery, machine learning is performed using samples that associate features measured in biological materials, such as the concentration of protein and a gene expression level, with labels indicating the presence or absence of a disease determined by a person like a doctor. Then, a small number of features that greatly influence the results of determining the presence or absence of the disease are extracted as biomarkers, and a model that generalizes the correlation between the biomarkers and the presence or absence of the disease is generated. Given newly measured values of the biomarkers as input, the model predicts the presence or absence of the disease.

See, for example, International Publication Pamphlet No. WO 2010/051320.

Machine learning may be performed using samples, each including measured features and a binary label such as "Yes" or "No," in order to generate a model for classifying inputs into two classes. However, the set of samples may include mixture samples having intermediate features between the two classes due to some circumstances in a process of preparing the samples. Such mixture samples become noise and may thus decrease the accuracy of results in the machine learning.

For example, in the biomarker discovery, samples with labels indicating the presence of a disease preferably indicate features measured in pure abnormal cells. However, collected abnormal cells may include normal cells and may also include somewhat abnormal cells with disease progression. In this case, mixture samples are obtained, which indicate intermediate features between features of pure abnormal cells and features of pure normal cells. Such mixture samples make it difficult to clearly classify inputs into a disease class and a non-disease class, which may lead to a risk of missing useful biomarkers.

SUMMARY

According to one aspect, there is provided a non-transitory computer-readable recording medium that causes a computer to perform a process including: classifying a plurality of samples into three or more clusters according to a feature amount of each of the plurality of samples, the plurality of samples each including the feature amount and a label indicating one of a first value and a second value; combining some clusters among the three or more clusters to form a combined cluster, based on information on a number of samples with labels indicating the first value among the plurality of samples; calculating an accuracy level of each of the plurality of samples with respect to the first value or the second value, based on a result of classifying the plurality of samples into the combined cluster and one or more remaining clusters after the combining among the three or more clusters; and performing machine learning using samples with accuracy levels not meeting a prescribed condition more preferentially than samples with accuracy levels meeting the prescribed condition among the plurality of samples.

The object and advantages of the invention will be realized and attained by means of the elements and combinations particularly pointed out in the claims.

It is to be understood that both the foregoing general description and the following detailed description are exemplary and explanatory and are not restrictive of the invention.

BRIEF DESCRIPTION OF DRAWINGS

FIG. 4 illustrates an example of a sample table;

DESCRIPTION OF EMBODIMENTS

Several embodiments will be described below with reference to the accompanying drawings.

First Embodiment

A first embodiment will be described.

Figure 1:
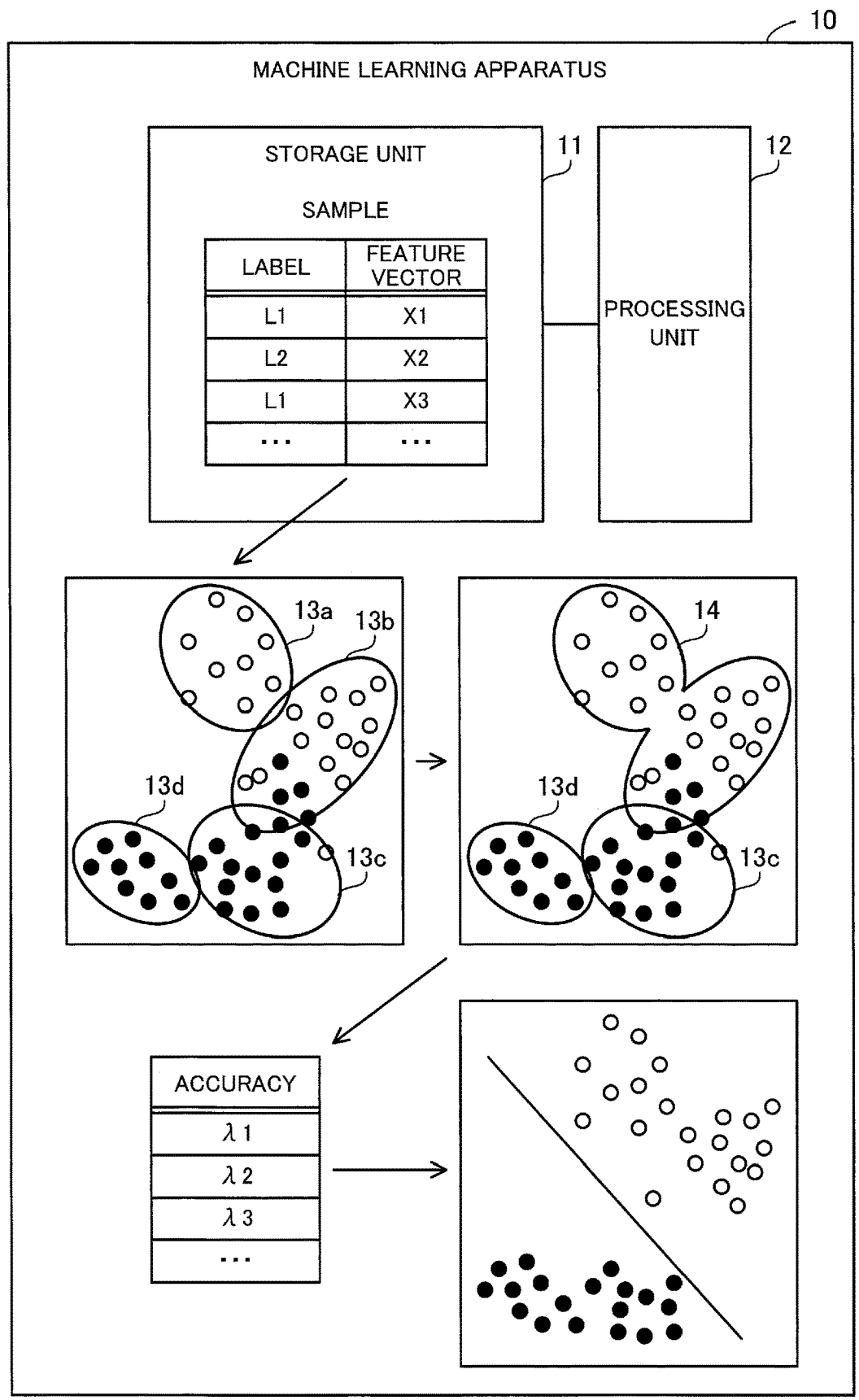
FIG. 1 is a view for explaining a machine learning apparatus according to a first embodiment.

FIG. 1 is a view for explaining a machine learning apparatus according to the first embodiment.

The machine learning apparatus 10 of the first embodiment performs machine learning using at least some of a plurality of samples as training data. In the machine learning of the first embodiment, the machine learning apparatus 10 generates a model for classifying inputs into two classes. For example, the machine learning apparatus 10 learns a medical diagnosis model that represents the correlation between features of biological materials and the presence or absence of disease. The machine learning apparatus 10 be used for discovering biomarkers that are features having a correlation with the presence. or absence of a disease. Note that the machine learning method of the first embodiment is applicable to data analysis not only in the medical fields but also in a variety of fields. The machine learning apparatus may be called an information processing apparatus or a computer. The machine learning apparatus 10 may be a client apparatus or a server apparatus.

The machine learning apparatus 10 includes a storage unit 11 and a processing unit 12. The storage unit 11 may be a volatile semiconductor memo device, such as a random access memory (RAM), or a non-volatile storage device, such as a hard disk drive (HDD) or a flash memory. The processing unit 12 is a processor such as a central processing unit (CPU), graphics processing unit (GPU), or a digital signal processor (DSP), for example. In this connection, the processing unit 12 may include an application-specific integrated circuit (ASIC), a field programmable gate array (FPGA), or another application-specific electronic circuit. The processor runs programs stored in a memory (this may be the storage unit 11). A set of multiple processors may be called "a multiprocessor" or simply "a processor."

The storage unit 11 stores therein a plurality of samples each including a label and one or more features. The samples may be called data records or data blocks. The labels are used as training data in the machine learning and are binary data indicating either a first value (L1) or a second value (L2). A label is manually given to each sample, for example. One of the first and second values indicates that a specific event is occurring ("Yes" and "On"), whereas the other indicates that the specific event is not occurring ("No" and "Off"). The features are numerical values measured in connection with a result indicated by a label. Each sample includes m features (m is an integer of one or more) and is represented by a point in an m-dimensional space. The features in each sample are represented by an m-dimensional vector (X1, X2, X3, or the like). This vector is referred to as "a feature vector," hereinafter.

In performing the biomarker discovery, the features are measurement values that are measured in biological materials, such as biological tissues and body fluid. For example, the features include the concentration of protein and a gene expression level. Gene expression is a process by which gene information is converted into functions of a biological body through the transfer of ribonucleic acid (RNA) or the synthesis of proteins. As the gene expression level, the concentration of mRNA of a target gene may be measured. A set of a relatively small number of features may be used as biomarkers, which serve as indicators having a correlation with the presence or absence of a particular disease. A label indicates the presence or absence of the disease. For example, the label indicates a result of diagnosis by a professional such as a doctor. For example, the first value indicates the absence of a disease and the second value indicates the presence of a disease. Samples with labels of the first value are expected to be data corresponding to normal biological materials without the disease. Samples with labels of the second value are expected to be data corresponding to abnormal biological materials with the disease.

Note that samples stored in the storage unit 11 include mixture samples having intermediate features between two classes due to some circumstances in a process of preparing the samples. In the case of medical data, for example, samples with labels indicating the presence of a disease preferably indicate features measured in pure abnormal cells, whereas samples with labels indicating the absence of a disease preferably indicate features measured in pure normal cells. However, collected abnormal cells may include normal cells and may also include somewhat abnormal cells with disease progression. In this case, mixture samples are obtained, which indicate intermediate features between features of pure abnormal cells and features of pure normal cells.

The use of a set of samples including mixture samples in machine learning may decrease the accuracy of a model for classifying inputs into two classes due to influence of the mixture samples. In the case of the biomarker discovery, there is a risk of missing useful biomarkers. To deal with this, the machine learning apparatus 10 performs preprocessing on machine learning data in order to reduce the influence of such mixture samples.

The processing unit 12 classifies a plurality of samples stored in the storage unit 11 into three or more clusters according to their feature vectors. Samples with similar feature vectors are grouped as one cluster. For this clustering, a variety of clustering algorithms including the k-means method and the Gaussian mixture model (GMM) may be used. The number of clusters may be fixed, may desirably be specified by a user, or may automatically be adjusted. Referring to the example of FIG. 1, the plurality of samples are classified into four clusters 13a, 13b, 13c, and 13d. In this connection, white points represent samples with labels of the first value (L1), whereas black points represent samples with labels of the second value (L2). The reason why there is an area where white points and black points coexist in the feature space is because mixture samples exist.

The processing unit 12 counts the number of samples with the labels of the first value (L1) among the plurality of samples stored in the storage unit 11. The processing unit 12 selects some of the above three or more clusters on the basis of information on the number of samples with the labels of the first value, and combines the selected clusters to form a combined cluster 14.

For example, the processing unit 12 selects the clusters to be combined to form the combined cluster 14 in such a manner that a prescribed percentage or more of the samples with the labels of the first value belong to the combined cluster 14. The prescribed percentage is preset to a value like 90%. The clusters to be combined are preferentially selected in ascending order of the distance to the center of a group of samples with the labels of the first value, that is, to the mean feature vector of the samples with the labels of the first value Referring to the example of FIG. 1, the clusters 13a and 13b among the clusters 13a, 13b, 13c, and 13d are combined to form the combined cluster 14.

The processing unit 12 computes the accuracy level of each sample with respect to the first value (L1) or the second value (L2), on the basis of the result of classifying the samples into the combined cluster 14 and the remaining clusters that are not combined. The accuracy level represents a result of evaluating the likelihood of a sample being a mixture sample, and is an estimated value of the closeness to a sample corresponding to the "pure" first value or to a sample corresponding to the "pure" second value. Although the accuracy level has a correlation with a label, it is an index different from the label. The accuracy level may also be considered to be a degree of mixture, a degree of pureness, a coexistence ratio, or another, considering that the accuracy level represents the likelihood of being a mixture sample. For example, the accuracy level is expressed as a real number ranging from 0 to 1, inclusive. In this case, the closer the accuracy level of a sample comes to 0.5, the more likely the sample is a mixture sample. For example, in the case of medical data, the accuracy level is an estimated value of closeness to a sample derived from pure normal cells or to a sample derived from pure abnormal cells. In this case, the accuracy level may also be considered to be a degree of normality, a degree of abnormality, a progress degree, or another.

For example, in the clustering, the processing unit 12 computes, for each sample, the probability of the sample belonging to each of the three or more clusters. The processing unit 12 then sums, for each sample, the probabilities for some cluster selected to form the combined cluster 14 among the probabilities for the three or more clusters, and sets the sum total probability (purity index) as the accuracy level. In this case, a sample with a feature vector closer to the combined cluster 14 has an accuracy level closer to 1, whereas a sample with a feature vector farther from the combined cluster 14 has an accuracy level closer to 0. Referring to the example of FIG. 1, the accuracy levels λ1, λ2, λ3, . . . are computed for the feature vectors X1, X2, X3, . . . , respectively.

The processing unit 12 performs machine learning, using samples whose accuracy levels do not meet a prescribed condition more preferentially than samples whose accuracy levels meet the prescribed condition among the plurality of samples stored in the storage unit 11. For example, the prescribed condition is that the accuracy level falls within a prescribed range indicating a high possibility of being a mixture sample. The prescribed range is set to a range excluding the maximum value and the minimum value and including the middle point (for example, 0.5) between the maximum value and minimum value, i.e., like a range of 0.2 to 0.8. Samples whose accuracy levels meet the prescribed condition are presumed to be mixture samples.

Here, as to the preferential use of samples whose accuracy levels do not meet the prescribed condition, the processing unit 12 may be designed to use, as training data in the machine learning, only samples whose accuracy levels do not meet the prescribed condition among the plurality of samples stored in the storage unit 11, excluding samples whose accuracy levels meet the prescribed condition.

Alternatively, the processing unit 12 may be designed to weight samples in such a manner that samples whose accuracy levels meet the prescribed condition are given weights that are smaller than those for samples that do not meet the prescribed condition. Then, the processing unit 12 may perform the machine learning using the plurality of samples stored in the storage unit 11 according to their weights. For example, it is considered that, when evaluating an error between an output of a model and a with respect to a sample with a small weight in the course of the machine learning, the processing unit 12 may provide less feedback of the error. The processing unit 12 may be designed to give a smaller weight to a sample as its accuracy level is closer to 0.5, and to give a higher weight to a sample as its accuracy level is further from 0.5. A weight of 0 may be given a sample whose accuracy level is 0.5. This means that samples with a weight of 0 are substantially excluded from training data and thus are: not used in the machine learning.

Referring to the example of FIG. 1, an accuracy level close to 0.5 is computed for each sample in an area where white point samples with the labels of the first value (L1) and black point samples with the labels of the second value (L2) coexist. These samples are presumed to have a high possibility of being mixture samples. Then, the samples are excluded from training data, and a model for classifying inputs into two classes is learned using the remaining samples.

As described above, the machine learning apparatus 10 of the first embodiment classifies a plurality of samples into three or more clusters according to their feature vectors. The machine learning apparatus 10 combines some clusters to form a combined cluster on the basis of the number of samples with labels of the first value, and computes the accuracy level of each sample on the basis of the result of classifying the samples into the combined cluster and the remaining clusters. The machine learning apparatus 10 then performs machine learning, using samples whose accuracy levels do not meet the prescribed condition more preferentially than samples whose accuracy levels meet the prescribed condition.

The above approach is able to reduce the influence of mixture samples that are obtained due to some circumstances in the process of preparing samples, in the machine learning. For example, in the case of medical data, the approach is able to reduce the influence of mixture samples that are obtained by sampling a cell group of normal cells and abnormal cells and by sampling cells with disease progression. This may improve the accuracy of results in the machine learning, such as improving the accuracy of a model for classifying inputs into two classes. The reason is as follows: if mixture samples and the other samples are treated equally, detection of a border between the two classes may become difficult due to the influence of the mixture samples, which increases a risk, of generating an improper model. In the case of performing the biomarker discovery using the machine learning, the first embodiment is able to reduce the risk, of missing useful biomarkers.

Second Embodiment

A second embodiment will now be described.

A machine learning apparatus of the second embodiment performs machine learning to discover biomarkers related to cancer. The machine learning apparatus may be a client apparatus or a server apparatus. The machine learning apparatus may be called a computer or an information processing apparatus.

Figure 2:
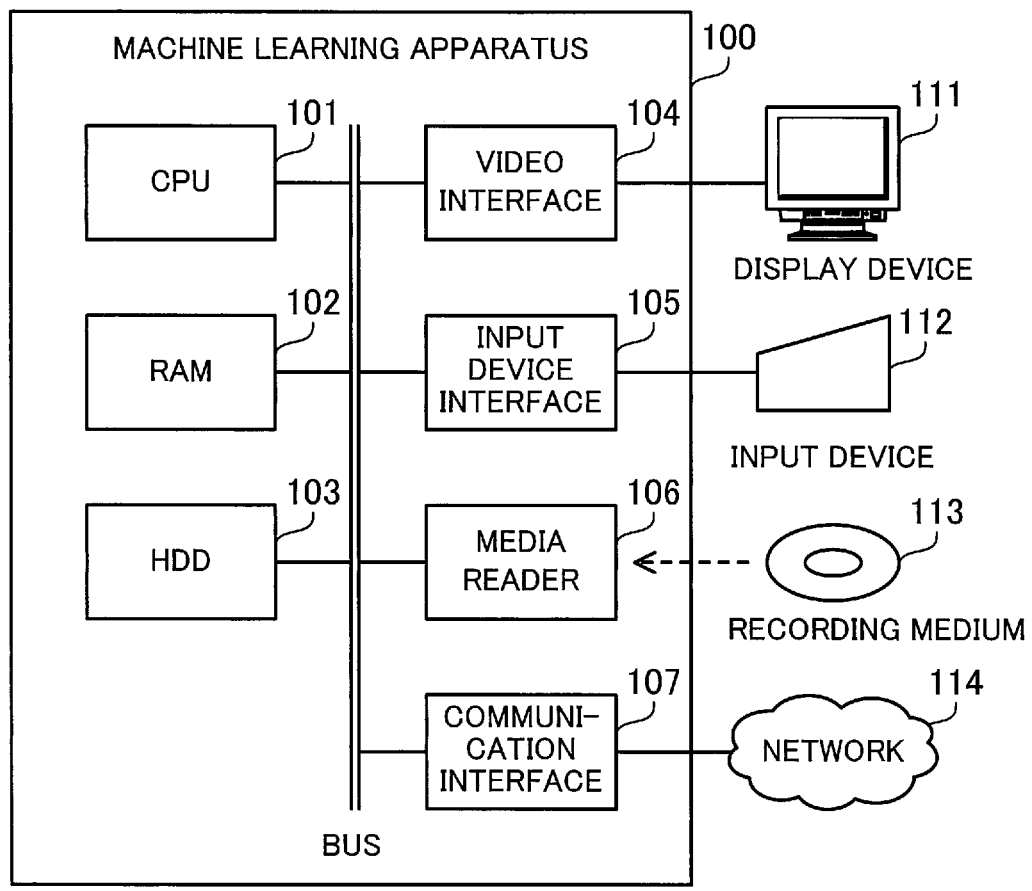
FIG. 2 illustrates an example of a hardware configuration of a machine learning apparatus according to a second embodiment.

FIG. 2 illustrates an example of a hardware configuration of a machine learning apparatus according to the second embodiment.

The machine learning apparatus 100 includes a CPU 101, a RAM 102, an HDD 103, a video interface 104, an input device interface 105, a media reader 106, and a communication interface 107. These units in the machine learning apparatus 100 are connected to a bus inside the machine learning apparatus 100. The machine learning apparatus 100 corresponds to the machine learning apparatus 10 of the first embodiment. The CPU 101 corresponds to the processing unit 12 of the first embodiment. The RAM 102 or the HDD 103 corresponds to the storage unit 11 of the first embodiment.

The CPU 101 is a processor that executes program instructions. The CPU 101 loads at least part of a program and data from the HDD 103 to the RAM 102 and executes the program. The CPU 101 may include plurality of processor cores, and the machine learning apparatus 100 may include a plurality of processors. A set of multiple processors may he called "a multiprocessor" or simply "a processor."

The RAM 102 is a volatile semiconductor memory device that temporarily stores therein programs to be executed by the CPU 101 or data to be used by the CPU 101 in processing. The machine learning apparatus 100 may include a different kind of memory device than RAM, or a plurality of memory devices.

The HDD 103 is a non-volatile storage device that stores therein software programs such as an operating system (OS), middleware, and application software, and data. The machine learning apparatus 100 may include a different kind of storage device such as a flash memory or a solid state drive (SSD), or a plurality of storage devices.

The video interface 104 outputs images to a display device 111 connected to the machine learning apparatus 100 in accordance with instructions from the CPU 101. Examples of the display device 111 include a cathode ray tube (CRT) display, a liquid crystal display (LCD), an organic electro-luminescence (OEL) display, a projector, and any desired kind of display device. Other than the display device 111, a printer or another output device may be connected to the machine learning apparatus 100.

The input device interface 105 receives an input signal from an input device 112 connected to the machine learning apparatus 100. Examples of the input device 112 include a mouse, a touch panel, a touch pad, a keyboard, and any desired kind of input device. A plurality of kinds of input devices may be connected to the machine learning apparatus 100.

The media reader 106 is a reading device that reads programs and data from a recording medium 113. Examples of the recording medium 113 include a magnetic disk, such as a flexible disk (FD) or an HDD, an optical disc, such as a compact disc (CD) or a digital versatile disc (DVD), a semiconductor memory device, and any desired kind of recording medium. For example, the media reader 106 copies a program or data read from the recording medium 113 into the RAM 102, HDD 103, or another recording medium. The read program is executed by the CPU 101, for example. In this connection, the recording medium 113 may be a portable recording medium and may be used for distribution of programs and data. In addition, the recording medium 113 and HDD 103 may be called computer-readable recording media.

The communication interface 107 is connected to a network 114 and communicates with other apparatuses over the network 114. The communication interface 107 may be a wired communication interface that is connected to a switch, a router, or another wired communication device or may be a wireless communication interface that is connected to a base station, access point, or another wireless communication device.

Figure 3:
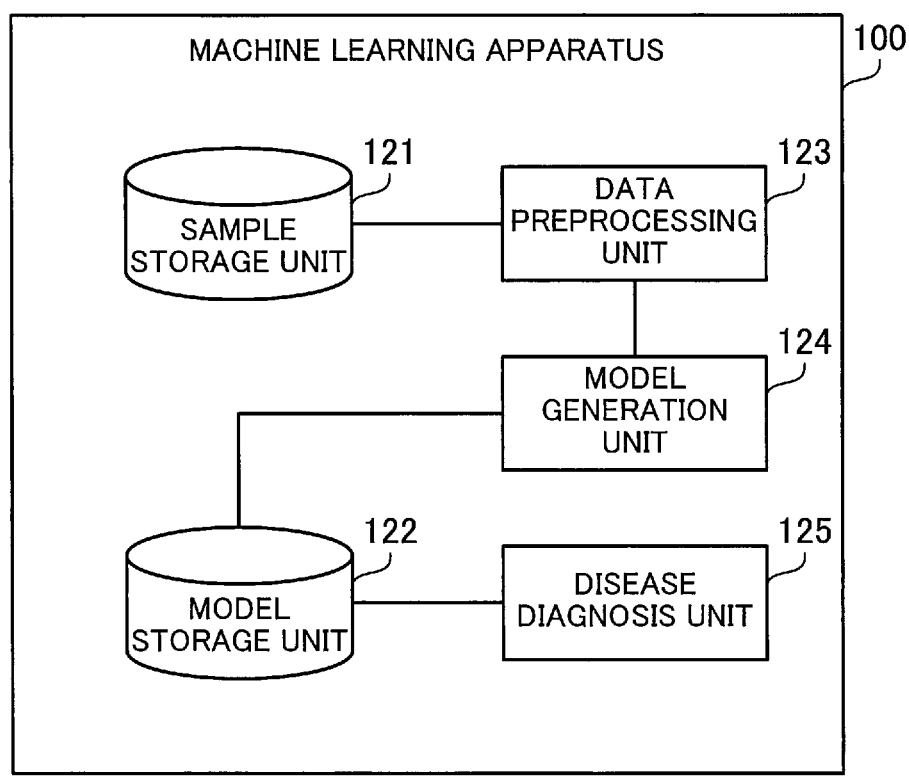
FIG. 3 is a block diagram illustrating an example of functions of the machine learning apparatus.

FIG. 3 is a block diagram illustrating an example of functions of the machine learning apparatus.

The machine learning apparatus 100 includes a sample storage unit 121, a model storage unit 122, a data preprocessing unit 123, a model generation unit 124, and a disease diagnosis unit 125. The sample storage unit 121 and model storage unit 122 are implemented by using a storage space in the RAM 102 or HDD 103, for example. The data preprocessing unit 123, model generation unit 124, and disease diagnosis unit 125 are implemented by the CPU 101 running programs, for example.

The sample storage unit 121 stores therein a plurality of samples prepared as machine learning data. Each sample corresponds to a biological tissue collected from a human and includes m features representing the gene expression levels of different genes measured in the same biological tissue. A very great number of features, like 10,000 features, may be included. The gene expression is a process by which gene information is converted into functions of a biological body through the transfer of RNA or the synthesis of proteins. As the gene expression level, the concentration of mRNA of target gene may be measured.

The plurality of samples include cancer samples each representing m gene expression levels measured in cancer cells of a cancer patient and normal samples each representing m gene expression levels measured in normal cells. Each sample is given a label indicating whether the sample is a normal sample or a cancer sample. The label indicates a result of diagnosis by a professional such as a doctor and is manually given. Labels may be considered to be flags since the labels have a choice between two values, i.e., a value indicating a normal sample and a value indicating a cancer sample, and is expressed by one bit having a value of "0" or "1." The labels are used as learning data in supervised machine learning.

Note that not all the m features indicated in each sample are related to cancer. The machine learning apparatus 100 performs machine learning using the above plurality of samples for biomarker discovery. The biomarker discovery is to detect a set of a small number of features related to cancer as biomarkers. There is a rough standard that the number of features to use as biomarkers is 20, less than or equal to 100, which is sufficiently less than the number of features included in each sample. A biomarker is a feature of a biological material and serves as an indicator having a correlation with the presence or absence of a particular disease or the progress of the disease. Biomarkers are used for diagnosis of a particular disease and confirmation of therapeutic effects. The machine learning apparatus 100 then performs machine learning to generate a model for determining. the presence or absence of cancer or the likelihood of cancer on the basis of values of the biomarkers. This model may be called a discrimination model, a prediction model, a determination model, a diagnosis model, or another.

The model storage unit 122 stores therein biomarker information indicating biomarkers detected by the machine learning. The biomarker information indicates a small number of genes (for example, as few as 20 genes) as biomarkers among the m genes. The model storage unit 122 also stores therein a model representing the correlation between values of the biomarkers and the presence or absence of cancer.

The data preprocessing unit 123 performs preprocessing on the plurality of samples stored in the sample storage unit 121. The data preprocessing unit 123 outputs a set of preprocessed samples as training data to the model generation unit 124. As will be described later, in the preprocessing, the data preprocessing unit 123 may exclude some of the plurality of samples stored in the. sample storage unit 121 from the training data. Alternatively, the data preprocessing unit 123 may give a weight to each of the plurality of samples stored in the sample storage unit 121. Some samples are given weights smaller than those for the other samples. The user may specify the preprocessing method. For example, the user may select one of exclusion of some samples and weighting of samples.

The model generation unit 124 obtains the training data from the data preprocessing unit 123 and performs machine learning using the obtained training data. The model generation unit 124 detects biomarkers for cancer through the machine learning, and generates a model for determining the presence or absence of cancer on the basis of values of the biomarkers, through the machine learning. The model generation unit 124 stores therein the biomarker information and the model in the model storage unit 122.

In the biomarker discovery, the model generation unit 124 tentatively generates, using all m features included in the samples of the training data, a model representing the correlation between the m features and the presence or absence of cancer. Then, on the basis of the generated model, the model generation unit 124 selects, from the m genes, a small number of genes that greatly influence the results of determining the presence or absence of cancer. For example, the model generation unit 124 selects a prescribed number of genes as biomarkers from the m genes, in descending order of the absolute value of their coefficients in the model. After determining the biomarkers, the model generation unit 124 generates a model representing the correlation between the biomarkers and the presence or absence of cancer, using the features corresponding to the biomarkers among the m features included in the samples of the training data.

In this connection, the model generation unit 124 may be designed to generate a model for the biomarker discovery and a model for the biomarker-based cancer diagnosis in a unified fashion. In addition, the model generation unit 124 may be designed to generate the biomarker information and the model with a procedure different from the above. For example, a considerable method is to repeatedly select a small number of features as biomarker candidates and generate a model representing the correlation between the selected features and the presence or absence of cancer until the generated model provides high accuracy.

For the machine learning, a machine learning algorithm, such as regression analysis or support vector machine (SVM), may be used. Here, a machine learning algorithm suitable for classification of inputs into two classes is preferable. In the case where the data preprocessing unit 123 excludes some samples from training data, the model generation unit 124 performs the machine learning using the other remaining samples. In the case where the data preprocessing unit 123 gives weights to the plurality of samples, the model generation unit 124 performs the machine learning, taking the weights into account. For example, when feeding back an error between an output of a model and a label with respect to a sample, the model generation unit 124 adjusts the error using the weight given to the sample. More specifically, as a sample is given a higher weight, greater feedback is provided regarding the error. As the sample is given a smaller weight, less feedback is provided regarding the error. That is, samples with small weights have small influence on the model to be learned.

The model generation unit 124 displays the result of the machine learning on the display device 111. For example, the model generation unit 124 displays biomarker information indicating the detected biomarkers on the display device 111. In this connection, the model generation unit 124 may display the result of the machine learning on an output device other than the display device 111 or may send the result to another information processing apparatus.

The disease diagnosis unit 125 receives user input for values of the biomarkers. The received values of the bi markers are different from the values of the samples stored the sample storage unit 121, and are gene expression levels measured in newly collected cells. The collected cells may be from a person who is taking cancer screening or from a cancer patient under treatment. Then, the disease diagnosis unit 125 enters the values of the biomarkers to the model stored in the model storage unit 122 and obtains the result of the cancer diagnosis from the model. The output of the model may be expressed by a discrete value indicating the presence or absence of cancer or a continuous value indicating the likelihood of cancer.

The disease diagnosis unit 125 display the result of the cancer diagnosis on the display device 111. The disease diagnosis unit 125 may output the result of the cancer diagnosis to an output device other than the display dunce 111 or send the result to another information processing apparatus. In the second embodiment, the machine learning apparatus 100 performs both the biomarker discovery and the cancer diagnosis using a model. Alternatively, one informa on processing apparatus may perform the biomarker discovery, and another may perform the cancer diagnosis using a model.

FIG. 4 illustrates an example of a sample table.

The sample table 126 is stored in the sample storage unit 121. The sample table 126 contains a plurality of samples each including a sample ID, m features, and a label. One row in the sample table 126 corresponds to a single sample. The sample may be called a data record or a data block.

The sample ID is identification information identifying a sample. The sample ID is an identification number of non-negative integer, for example. The sample table 126 contains therein p cancer samples with labels indicating the presence of cancer and c normal samples with labels indicating the absence of cancer. That is, the sample table 126 contains therein the p+c samples in total. The m features are m different gene expression levels measured in the same biological tissue. The label indicates the presence or absence of cancer. For example, a label of 1 indicates presence of cancer (patient or abnormal), whereas a label of 0 indicates absence of cancer (control or normal). Normal samples and cancer samples are measured in the same kind of biological tissues among lung, liver, colon and others.

The following describes problems of mixture samples and preprocessing for reducing the influence of the mixture samples.

Figure 5:
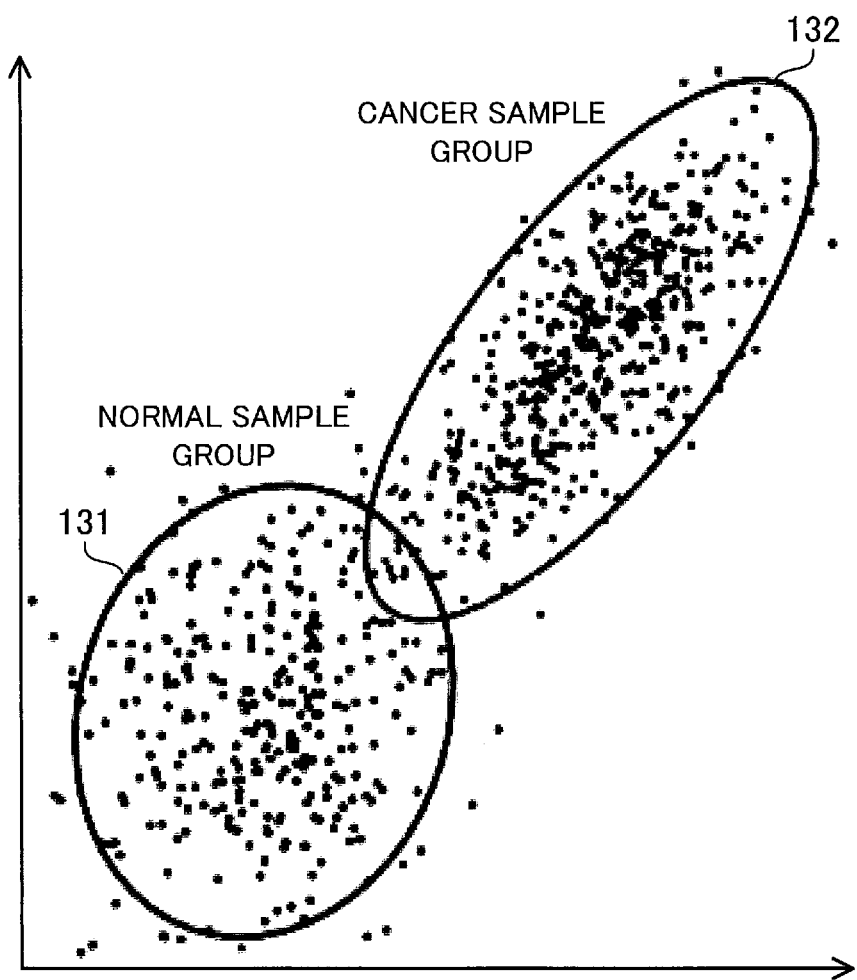
FIG. 5 is a graph illustrating an example of a sample distribution.

FIG. 5 is a graph illustrating an example of a sample distribution.

It is now considered that a plurality of samples contained in the sample table 126 are mapped to an m-dimensional feature space with m axes corresponding to m features. In the second embodiment, a two-dimensional feature space is illustrated for simple explanation.

When the plurality of samples are mapped to the feature space, a normal sample group 131 including normal samples with normal labels and a cancer sample group 132 including cancer samples with cancer labels are formed. The points of the plurality of normal samples are expected to be located close to each other, whereas the points of the plurality of cancer samples are expected to be located close to each other. The normal sample group 131 and the cancer sample group 132 are preferably clearly separate from each other. However, the normal sample group 131 and the cancer sample group 132 may overlap. That is, there may be an area where the points of normal samples and the points of cancer samples coexist. This is because so-called mixture samples exist.

Mixture samples occur depending on collected biological tissues. Normal samples are preferably derived from pure normal cells, and cancer samples are preferably derived from pure cancer cells. However, in actual, collected cancer cells may include normal cells and may also include cells with cancer progression. From such cells, mixture samples having intermediate features between pure normal cells and pure cancer cells are generated.

If machine learning is performed while treating all samples including mixture samples equally, it would be difficult to detect a clear border between the normal sample group 131 and the cancer sample group 132. Especially, in the SVM, if samples with different labels exist around a border, it would be difficult to detect the border correctly. This decreases the accuracy of classification by a generated model and thus it would be difficult to discover biomarkers.

Figure 6:
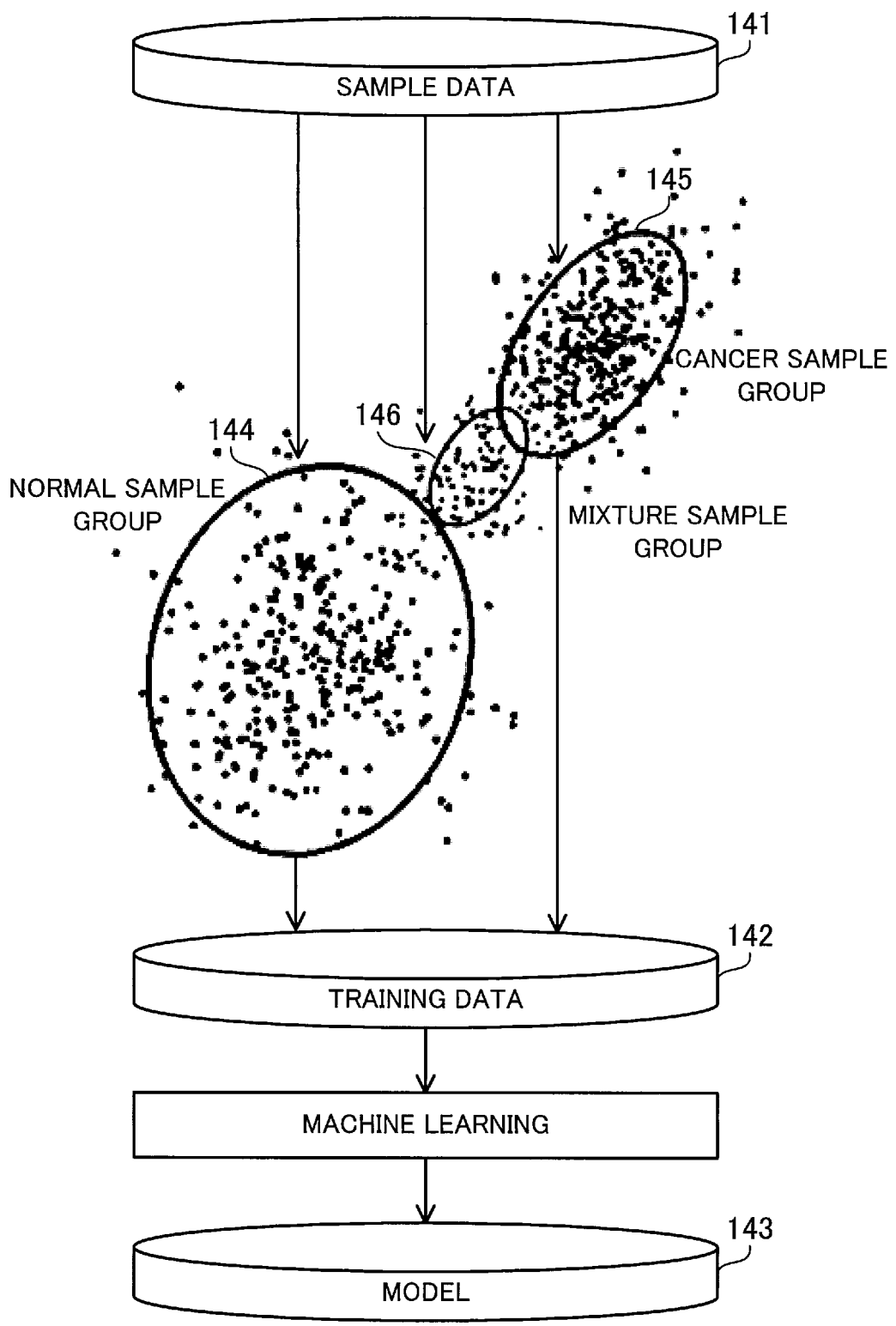
FIG. 6 illustrates an example of excluding mixture samples.

To deal with the above, the machine learning apparatus 100 is designed to automatically presume some of a plurality of samples to be mixture samples and reduce the influence of the mixture samples on the machine learning. More specifically, the machine learning apparatus 100 is designed to exclude the mixture samples from training data or gives the mixture samples weights smaller than those for the other samples FIG. 6 illustrates an example of excluding mixture samples.

The following describes a case of excluding mixture samples as data preprocessing.

The data preprocessing unit 123 classifies sample data 141 into a normal sample group 144, a cancer sample group 145, and a mixture sample group 146. The sample data 141 is a set of samples contained in the sample table 126.

The mixture sample group 146 is a set of samples presumed to be mixture samples. The normal sample group 144 is a set of samples excluding the samples classified into the mixture sample group 146 among samples with normal labels. The samples belonging to the normal sample group 144 are presumed to be samples from pure normal cells. The cancer sample group 145 is set of samples excluding the samples classified into the mixture sample group 146 among samples with cancer labels. The samples belonging to the cancer sample group 145 are presumed to be samples from pure cancer cells.

The data preprocessing unit 123 excludes the samples of the mixture sample group 146 from the sample data 141, and generates training data 142 from the samples of the normal sample group 144 and the cancer sample group 145. The model generation unit 124 performs machine learning using the training data 142 to generate a model 143. This machine learning is to detect a border between the samples with the normal labels and the samples with the cancer labels, ignoring the mixture samples.

In the second embodiment, to extract the mixture samples, a purity parameter λ is computed as a hidden variable with respect to each sample. The purity parameter λ is an index that indicates how likely a sample is regarded as a sample from pure normal cells. The purity parameter λ may be interpreted as an estimated value of the percentage of normal cells included in a collected biological tissue. In view of this, the purity parameter λ may also be interpreted as a coexistence ratio, a mixed degree, an accuracy level, a pure degree, or another. The purity parameter λ may also be interpreted as representing the nonprogress degree of cancer. In view of this, the purity parameter λ may also be called a nonprogress degree.

The purity parameter λ is a real number ranging from 0 to 1, inclusive. The closer the purity parameter λ of a sample comes to 1, the more likely the sample is a sample from pure normal cells. The closer the purity parameter λ of a sample comes to 0, the more likely the sample is a sample from pure cancer cells. The closer the purity parameter λ of a sample comes to 0.5, the more likely the sample is a mixture sample. Although the purity parameter λ has a high correlation with a label, it is an index different from the label.

The following describes a method of computing the purity parameter λ and a method of extracting mixture samples.

First, the data preprocessing unit 123 scales the features of samples. For example, the data preprocessing unit 123 performs numerical transformation in such a manner that, with respect to each gene, values of the gene expression level are distributed within a certain numerical range while the features of the samples keep their magnitude. relationship. In addition, the data preprocessing unit 123 reduces the dimensions of the feature space so as to reduce the dimensions of the feature vectors from about 10,000 to about 100. For this reduction of dimensions, the singular value decomposition (SVD) may be used, for example. This reduction of dimensions makes it possible to reduce the number of dimensions in the feature space while keeping the distance relationships between the samples in the feature space as much as possible. The scaling of features and the reduction of dimension are implemented by numerical transformation temporarily performed for extraction of mixture samples.

Next, the data, preprocessing unit 123 performs clustering to classify samples into a plurality of clusters according to their positions in the feature space after the reduction of dimensions. This clustering is to classify samples located close to each other into the same cluster and samples located farther from each other into different clusters. The number n of clusters determined in advance. For example, the number of clusters is set to five. For the clustering, a variety of clustering algorithms may be used, such as the k-means clustering and the Gaussian mixture model. The second embodiment uses the Gaussian mixture model for the clustering.

In the Gaussian mixture model, an overlap of n Gaussian distributions corresponding to n clusters in a feature space is seen as probabilistic generation of a set of current samples. The Gaussian mixture model defines a generation probability P expressed as an equation (1) for each sample, and determines parameters for the n clusters such as to maximize the total generation probability P of all samples.

In the equation (1), $x_i$ denotes the feature vector of the i-th sample among the p+c samples and corresponds to the position of the sample in the feature space. $\mu_l$ denotes the center vector of the l-th cluster among the n clusters and corresponds to the center position of the cluster in the feature space. $\sigma_l$ represents the standard deviation of the l-th cluster among the n clusters and corresponds to the size of the cluster in the feature space. In this connection, the size of the cluster is not always correlated with the number of members in the cluster. $\pi_{il}$ represents a belonging proportion that is a probability chat the i-th sample belongs to the l-th cluster. The Gaussian mixture model computes, as a proportion, which cluster each sample belongs to. The belonging proportion $\pi_{il}$ is a real number ranging from 0 to 1, inclusive, and meets the constraint defined by the equation (2). That is, the total belonging proportion of each sample to the n clusters is one. $C_l$ is a scaling parameter that is applied to the l-th cluster among the n clusters. The scaling parameter $C_l$ is computed depending on the standard deviation $\sigma_l$ of the l-th cluster.

The generation probability P of a sample represents a probability of generating the sample in an assumed overlap of n Gaussian distributions. The clustering using the Gaussian mixture model is defined as an optimization problem that maximizes the total generation probability P of all the samples by varying the center vector $\mu_l$, standard deviation $\sigma_l$, and belonging proportion $\pi_{il}$. To solve this optimization problem, a hidden variable indicating tentative selection of one of the clusters each sample belongs to may be introduced. In this case, each sample is tentatively classified into one of the n clusters. On the basis of the classification result, the center vector $\mu_l$ and standard deviation $\sigma_l$ are updated with respect to each of the n clusters. Then, classification of each sample to a cluster is reviewed on the basis of the updated center vector $\mu_l$ and standard deviation $\sigma_l$. This process is repeated until an increase in the total generation probability P converges.

$$P(\vec{x_i}) = \sum_{\ell=1}^{n} \pi_{i\ell} C_\ell \exp\left(-\left(\frac{\vec{x_i} - \vec{\mu_\ell}}{\sigma_\ell}\right)^2\right) \quad (1)$$

$$\sum_{\ell=1}^{n} \pi_{i\ell} = 1 \quad (2)$$

After that, the data preprocessing unit 123 computes, as a mean vector $x_v$, the mean of feature vectors of the c samples with the normal labels among the p+c samples. The data preprocessing unit 123 sorts the n clusters in ascending order of the distance of their center vectors $\mu_l$ to the mean vector $x_v$. In addition, the data preprocessing unit 123 determines, for each sample, one cluster to which the sample belongs with the highest possibility. The one cluster here is a cluster corresponding to the highest belonging proportion $\pi_{i1}$ of the sample. The data preprocessing unit 123 counts, for each of the n clusters, the number of samples with the normal labels belonging to the cluster.

The data preprocessing unit 123 preferentially selects one of the n clusters in ascending order of the distance of their center vectors $\mu_l$ to the mean vector $x_v$, and classifies the selected cluster as a "normal cluster." The data preprocessing unit 123 sums the numbers of samples with the normal labels belonging to one or more clusters classified as normal clusters, and computes the percentage of the sum total number of samples to the total number c of samples with the normal, labels, as a normal coverage. The data preprocessing unit 123 repeats the above classification as a normal cluster until the normal coverage becomes higher than or equal to a prescribed threshold (for example, 90%). By doing so, $n_n$ clusters among the n clusters are classified as normal clusters, and the remaining $n_a$ ($=n-n_n$) clusters are classified as abnormal clusters.

Then, the data preprocessing unit 123 sums, for each sample, the belonging proportions to the $n_n$ normal clusters among the belonging proportions $\pi_{il}$ to the n clusters, and, takes the sum total belonging proportion as a purity parameter $\lambda$. Through the clustering, the belonging proportion vector $\pi_i$ expressed by the equation (3) is computed with respect to the i-th sample. The purity parameter $\lambda_i$ of the i-th sample is defined as the equation (4), where N denotes a set of normal clusters.

$$\pi_i = (\pi_{i1}, \pi_{i2}, \ldots, \pi_{in}) \quad (3)$$

$$\lambda_i = \sum_{\ell \in N} \pi_{i\ell} \quad (4)$$

The data preprocessing unit 123 compares the purity parameter $\lambda$ of each sample with a prescribed numerical range excluding the maximum value of 1 and the minimum value of 0 and including the central value of 0.5. The prescribed numerical range is previously set to a prescribed range, like a range of 0.2 to 0.8, inclusive. The data preprocessing unit 123 presumes samples with purity parameters $\lambda$ falling within the prescribed numerical range to be mixture samples, and classifies these samples into the mixture sample group M. The data preprocessing unit 123 generates training data, excluding the samples classified into the mixture sample group M among the p+c samples. Alternatively, the data preprocessing unit 123 may be designed to give a weight to each of the p+c samples according to its purity parameter $\lambda$.

In the weighting, samples belonging to the mixture sample group M are given weights smaller than those for the other samples. It is considered that a smaller weight is given to a sample whose purity parameter $\lambda$ is closer to 0.5. For example, the i-th sample is given a weight $w_i$ ($=|\lambda_i - 0.5| \times 2$), i.e., the double of the, absolute value of the difference between the purity parameter $\lambda$ and 0.5. In this case, a sample with the purity parameter $\lambda$ of 1 is given a weight of 1, whereas a sample with the purity parameter $\lambda$ of 0 is given a weight of 1, and a sample with the purity parameter $\lambda$ of 0.5 is given a weight of 0.

In this connection, the second embodiment defines, as an index for extracting mixture samples, the purity parameter $\lambda$ indicating the likelihood of being a normal sample. Alternatively, a degree of abnormality $\lambda'$ ($=1-\lambda$) indicating the likelihood of being an abnormal. sample may be. defined. In addition, the second embodiment classifies samples into a normal cluster in ascending order of the distance to the mean vector of samples with the normal labels, and classifies the remaining samples into an abnormal cluster according to the normal coverage. Alternatively, it may be so designed chat samples are classified into an abnormal cluster in ascending order of the distance to the mean vector of samples with cancer labels, and the remaining samples are classified into a normal cluster according to an abnormal coverage. In addition, the total belonging proportion to the abnormal cluster may be computed as a degree of abnormality $\lambda'$. In the second embodiment, "normality" and "abnormality" have a symmetrical relationship and it is an objective to extract mixture samples falling in an intermediate state between the "normality" and the "abnormality". Therefore, the above process of extracting mixture samples may be modified, utilizing the symmetrical relationship between the normality and the abnormality.

Figure 7:
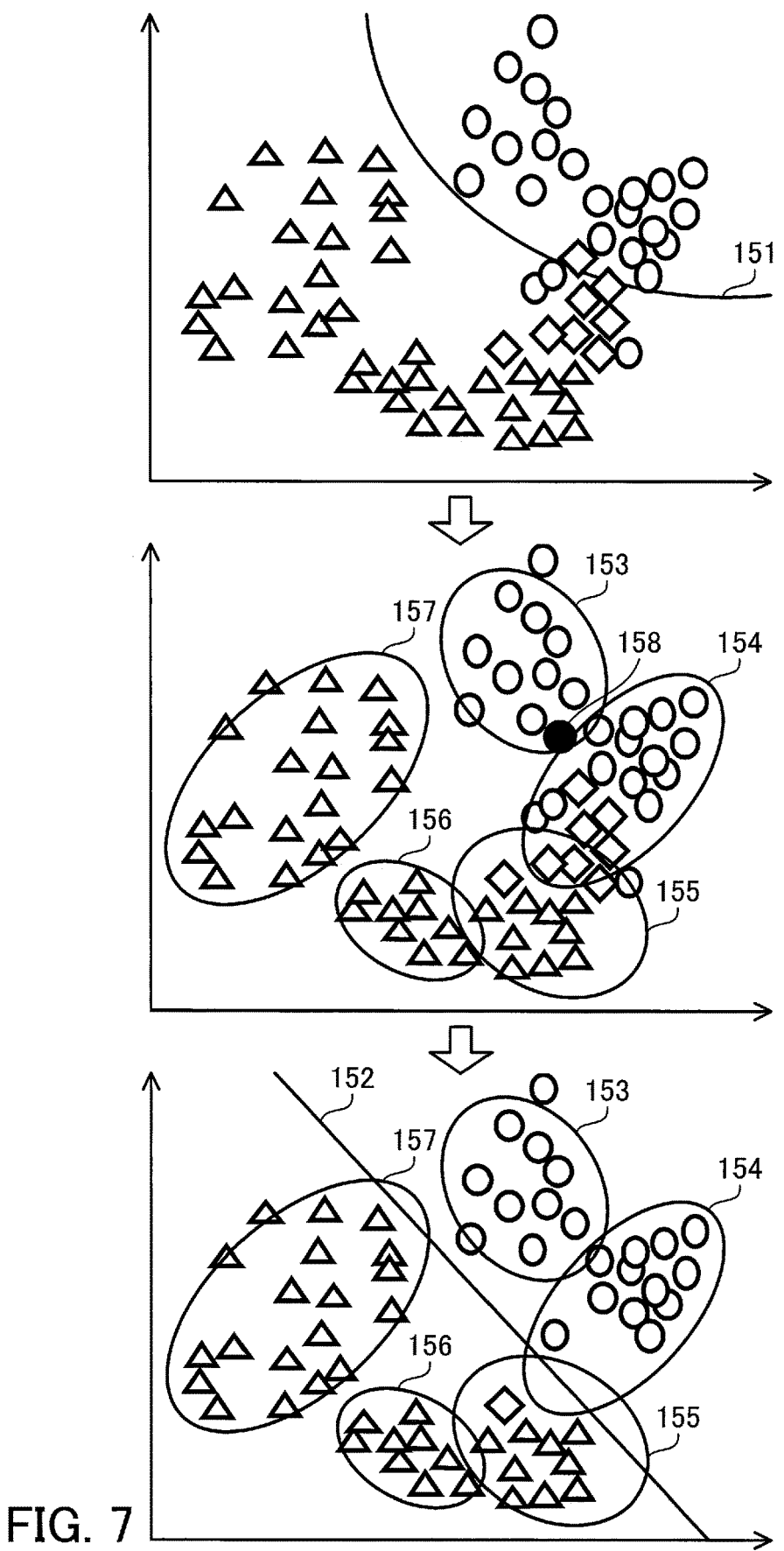
FIG. 7 illustrates another example of excluding mixture samples.

FIG. 7 illustrates another example of excluding mixture samples.

The following describes a case of excluding mixture samples as data preprocessing. In FIG. 7, normal samples are represented by circle marks, mixture samples are represented by rhombus marks, and cancer samples are represented by triangle marks. The normal samples in FIG. 7 are samples with normal labels. The mixture samples in FIG. 7 are samples objectively seen as mixture samples, such as samples derived from mixtures of normal cells and abnormal cells and samples with cancer progression, among the samples with cancer labels. The cancer samples in FIG. 7 are samples ocher than the mixture samples among the samples with the cancer labels. In this connection, the machine learning apparatus 100 is not able to acquire objective information as to whether a sample with a cancer label is a mixture sample or not.

If the machine learning is performed while treating all samples equally, a model that divides the feature space by a border line 151 is generated. Computation of the border line 151 is greatly influenced by the mixture samples. Thus, the border line 151 is considered to be inappropriate.

By contrast, the second embodiment generates five clusters 153, 154, 155, 156, and 157 in the feature space. In addition, the mean vector 158 of the samples with the normal labels is computed. Then, clusters are selected in ascending order of the distance to the mean vector 158. In this example, the clusters 153 and 154 are selected in this order and are classified as normal clusters. The clusters 153 and 154 cover most of the normal samples. Therefore, the remaining clusters 155, 156, and 157 are classified as abnormal clusters.

Then, for each sample, the total belonging proportion to the clusters 153 and 154 is computed as a purity parameter λ. Referring to FIG. 7, many of the mixture samples are located close to the border between the cluster 154 classified as the normal cluster and the cluster 155 classified as the abnormal cluster. The belonging proportion to the cluster 154 is added to the purity parameter λ, but the belonging proportion to the cluster 155 is not added to the purity parameter λ. Therefore, many mixture samples have a purity parameter λ close to 0.5. As a result, most of the mixture samples in FIG. 7 are excluded from training data.

In the case of performing the machine learning using such training data, a model that divides the feature space by a borderline 152 is generated. Although the mixture samples may become noise, the border line 152 is computed without influence of most of the mixture samples and is said to be an appropriate border line. Therefore, it becomes possible to detect useful biomarkers and thus to improve the accuracy of discrimination by a model for discriminating between the presence and the absence of cancer on the basis of values of the biomarkers.

In this connection, the second embodiment generates a model using all of samples that do not belong to at least the mixture sample group M. Alternatively, cancer samples may be classified into a plurality of subgroups, and a model may be generated using all normal samples and cancer samples belonging to one of the subgroups. Thereby, a plurality of models respectively corresponding to the plurality of subgroups may be generated. This is useful for the case where cancer cells have different features according to the progress of cancer. That is, different discrimination models are generated according to different progresses. In this case, instead of equally treating all remaining clusters other than the above-described normal clusters as abnormal clusters, the remaining clusters may be each treated as a subgroup of cancer samples.

The following describes how the machine learning apparatus 100 operates.

Figure 8:
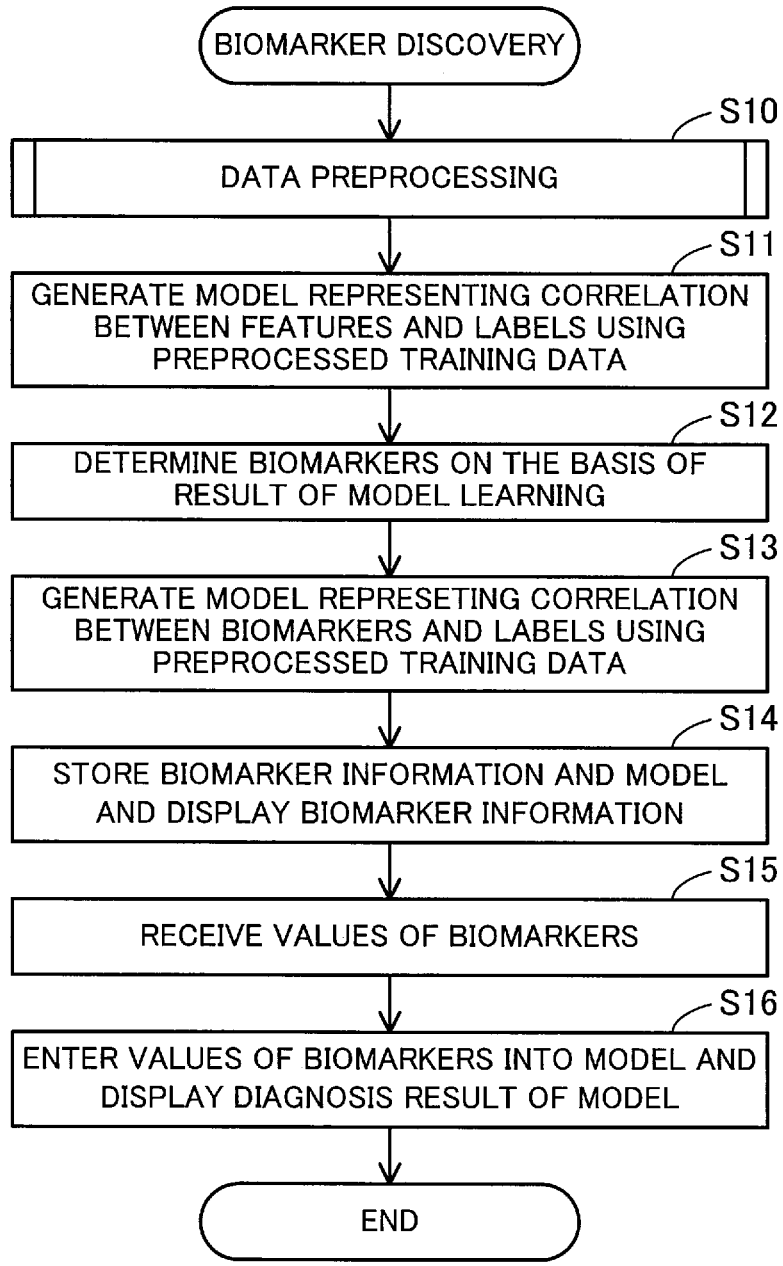
FIG. 8 is a flowchart illustrating how to perform biomarker discovery.

FIG. 8 is a flowchart illustrating how to perform biomarker discovery.

(S10) The data preprocessing unit 123 performs preprocessing on a plurality of samples contained in the sample table 126 stored in the sample storage unit 121, and supplies preprocessed training data to the model generation unit 124. The data preprocessing will be described in detail later.

(S11) The model generation unit 124 generates a model representing the correlation between m features and labels, using the preprocessed training data. For example, the model generation unit 124 generates an SVM model for classifying samples into the presence of cancer and the absence of cancer on the basis of m gene expression levels.

(S12) The model generation unit 124 determines biomarkers on the basis of the result of the model learning of step S11. For example, the model generation unit 124 selects, from the m coefficients corresponding to the m gene expression levels in the model, a prescribed number (for example, about 20) of coefficients in the model in descending order of their absointe values, and determines a set of genes corresponding to the selected coefficients as biomarkers.

(S13) The model generation unit 124 generates a model representing the correlation between the biomarkers and labels using the preprocessed training data. For example, the model generation unit 124 extracts the gene expression levels of the biomarkers among the m gene expression levels from each sample of the training data, and generates an SVM model for classifying samples into the presence of cancer and the absence of cancer on the basis of the gene expression levels of the biomarkers.

(S14) The model generation unit 124 stores biomarker information indicating the determined biomarkers, such as the identification information of genes included in the biomarkers, in the model storage unit 122. In addition, the model generation unit 124 stores the model representing the correlation between the biomarkers and the labels, generated at step S13, in the model storage unit 122. The model generation unit 124 displays the biomarker information on the display device 111. The model generation unit 124 may display the model representing the correlation between the biomarkers and the labels on the display device 111.

(S15) The disease diagnosis unit 125 receives user input for values of the biomarkers. The values of the biomarkers are a prescribed number of gene expression levels included in the biomarkers.

(S16) The disease diagnosis unit 125 reads the model from the model storage unit 122 and enters the values of the biomarkers received. at step S15 into the model. The disease diagnosis unit 125 obtains a diagnosis result indicating the presence or absence of cancer or the, likelihood of cancer from the model. The disease diagnosis unit 125 displays the diagnosis result of the model on the display device 111.

Figure 9:
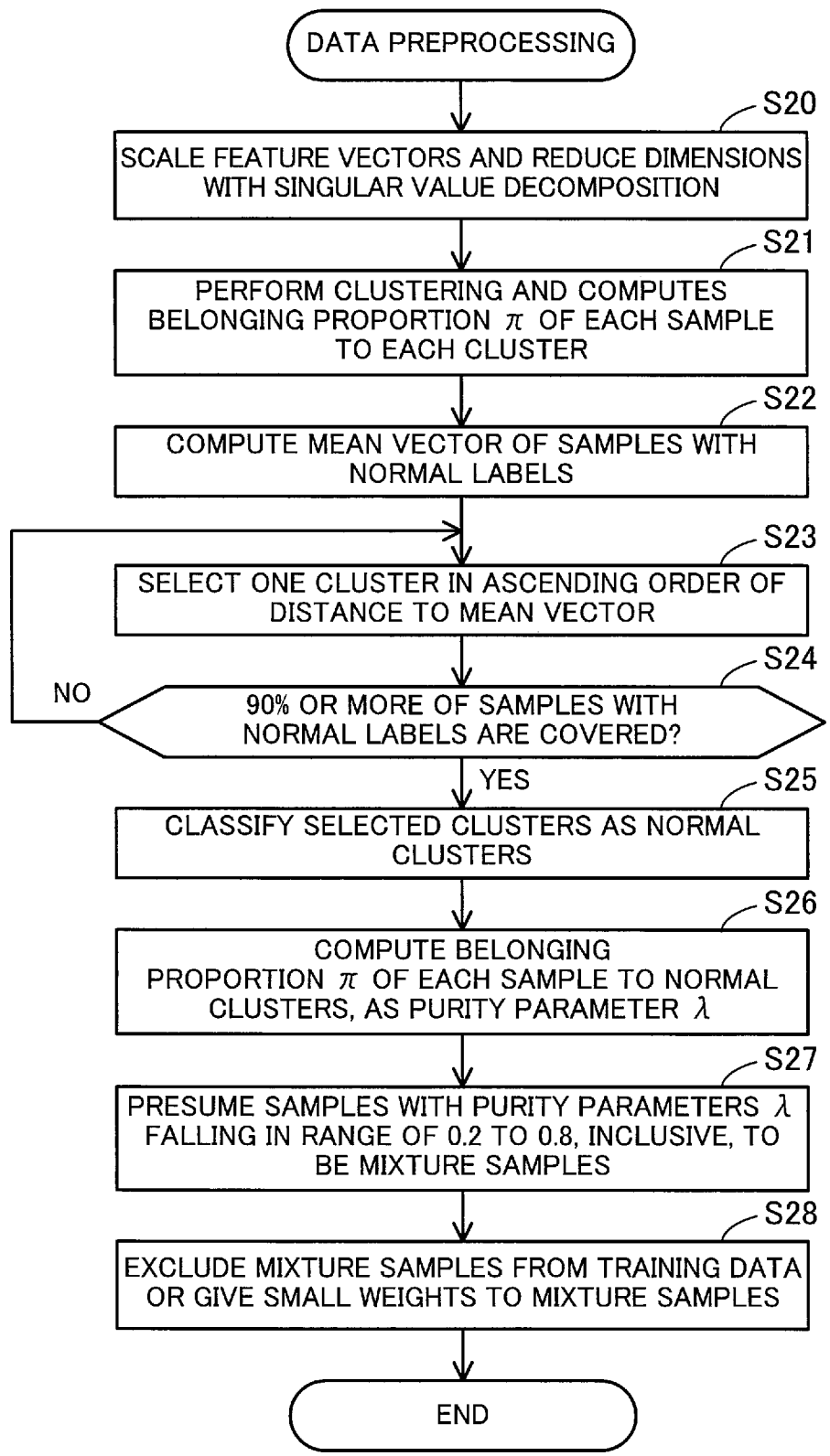
FIG. 9 is a flowchart illustrating how to perform data preprocessing.

FIG. 9 is a flowchart illustrating how to perform data preprocessing.

The data preprocessing is performed at the above-described step S10.

(S20) The data preprocessing unit 123 scales the feature vectors of the plurality of samples contained in the sample table 126. For example, the data preprocessing unit 123 performs numerical transformation in such a. manner that, with respect to each gene, values of the gene expression level are distributed within a prescribed. numerical range. In addition, the data preprocessing unit 123 reduces the number of dimensions in the feature space with the singular value decomposition. For example, the data preprocessing unit 123 reduces the number of features from about 10,000 to about 100.

(S21) The data preprocessing unit 123 performs clustering on the plurality of samples on the basis of their feature vectors obtained after the scaling and the reduction of dimensions performed at step S20. For example, the Gaussian mixture model may he employed for the clustering. The clustering generates a prescribed number of clusters and computes, for each sample, the belonging proportion n of the sample to each of the clusters.

(S22) The data preprocessing unit 123 computes the mean of the feature vectors of the samples with the normal labels among the plurality of samples, to obtain a mean vector.

(S23) The data preprocessing unit 123 selects one of the clusters generated at step S21, in ascending order of the distance of their center vectors to the mean vector of step S22.

(S24) The data preprocessing unit 123 determines whether the selected one or more clusters cover 90% or more of the samples with the normal labels. If the selected one or more clusters cover 90% or more, the process proceeds to step S25. Otherwise, the process proceeds back to step S23.

(S25) The data preprocessing unit 123 classifies the one or more clusters selected at step S23 as normal clusters and the other clusters as abnormal clusters.

(S26) The data preprocessing unit 123 computes the total belonging proportion n of each sample to the clusters classified as the normal clusters, as a purity parameter λ.

(S27) The data preprocessing unit 123 searches for samples whose purity parameters λ fall in a range of 0.2 to 0.8, inclusive, and presumes the found samples to be mixture samples.

(S28) The data preprocessing unit 123 excludes the mixture samples recognized at step S27 from the plurality of samples contained in the sample table 126, and generates training data from the remaining samples. Alternatively, the data preprocessing unit 123 gives a weight to each of the plurality of samples contained in the sample table 126 according to the purity parameter λ computed at step S27. A smaller weight is given to a sample whose purity parameter λ is closer to 0.5, and a higher weight is given to a sample whose purity parameter λ is further from 0.5. This means that small weights are given to the mixture samples recognized at step S27. The data preprocessing unit 123 generates training data that includes all samples contained in the sample table 126 and given weights. Then, the data preprocessing unit 123 supplies the training data to the model generation unit 124.

As described above, the machine learning apparatus 100 of the second embodiment performs machine learning using a plurality of samples each including a great number of gene expression levels and a label indicating the presence or absence of cancer, in order to detect a set of a small number of genes having a correlation with the presence or absence of cancer, as biomarkers. In addition, the machine learning apparatus 100 generates a model representing the correlation between values of the biomarkers and the presence or absence of cancer. As a result, it becomes possible to diagnose cancer and evaluate the effects of cancer therapy using the biomarkers.

In addition, the machine learning apparatus 100 computes, for each sample, the purity parameter representing the likelihood of being a normal sample on the basis of a distribution of feature vectors of the plurality of samples. Then, the machine learning apparatus 100 presumes samples with purity parameters closer to 0.5 to be mixture samples. The machine learning apparatus 100 performs data preprocessing so as to reduce they influence of the mixture samples on the machine learning. For example, the mixture samples are excluded from training data or the mixture samples are given weights smaller than those for the other samples. By doing so, it becomes possible to reduce uncertainty of a border between the normal samples and the cancer samples due to the influence of the mixture samples and to improve the accuracy of discrimination by the model for discriminating between the presence and the absence of cancer on the basis of values of biomarkers. This leads to an increase in the possibility of success in the biomarker discovery for detecting biomarkers having a correlation with cancer.

According to one aspect, the accuracy of results of machine learning is improved.

All examples and conditional language provided herein are intended for the pedagogical purposes of aiding the reader in understanding the invention and the concepts contributed by the inventor to further the art, and are not to be construed as limitations to such specifically recited examples and conditions, nor does the organization of such examples in the specification relate to a showing of the superiority and inferiority of the invention. Although one or more embodiments of the present invention have been described in detail, it should be understood that various. changes, substitutions, and alterations could be made hereto without departing from the spirit and scope of the invention.

What is claimed is:

1. A non-transitory computer-readable recording medium that causes a computer to perform a process comprising:
   classifying a plurality of samples into three or more clusters according to a feature amount of each of the plurality of samples, the plurality of samples each including the feature amount and a label indicating one of a first value and a second value;
   combining some clusters among the three or more clusters to form a combined cluster, based on information on a number of samples with labels indicating the first value among the plurality of samples;
   calculating an accuracy level of each of the plurality of samples with respect to the first value or the second value, based on a result of classifying the plurality of samples into the combined cluster and one or more remaining clusters after the combining among the three or more clusters; and
   performing machine learning using samples with accuracy levels not meeting a prescribed condition more preferentially than samples with. accuracy levels meeting the prescribed condition among the plurality of samples.

2. The non-transitory computer-readable recording medium according to claim 1, wherein the prescribed condition is that the accuracy level falls in prescribed numerical range excluding a ma value and a minimum value for the accuracy level and including a middle point between the maximum value and the minimum value.

3. The non-transitory computer readable recording medium according to claim 1, wherein the machine learning includes excluding the samples with the accuracy levels meeting the prescribed condition from the plurality of samples.

4. The non-transitory computer-readable recording medium according to claim 1, wherein the machine learning includes giving first weights to the samples with the accuracy levels meeting the prescribed condition, the fist weights being smaller than second weights to be given to the samples with the accuracy levels not meet of the prescribed condition.

5. The non-transitory computer-readable recording medium according to claim 1, wherein;
   the machine learning includes generating model representing correlation between the feature amount and the label; and
   the process further includes receiving a new feature amount and deciding the first value or the second value for the received new feature amount using the model.

6. The non-transitory computer-readable recording medium according to claim 1, wherein forming of the combined cluster includes selecting the some clusters among the three or more clusters in such a manner that a prescribed percentage or more of the samples with the labels indicating the first value belong to the combined cluster.

7. The non-transitory computer readable recording medium according to claim 1, wherein:
   the classifying into the three or more clusters includes calculating, for each of the plurality of samples, a probability that the each sample belongs to each of the three or more clusters; and
   the calculating of the accuracy level includes calculating, as the accuracy level with respect to the first value, sum of probabilities for the some clusters among probabilities for the three or more clusters.

8. The non-transitory computer-readable recording medium according to claim 1, wherein:
the feature amount includes a measurement value measured in a biological material;
the first value indicates absence of a disease and the second valve indicates presence of the disease; and
the machine learning includes presuming the samples with the accuracy levels meeting the prescribed condition to be mixture samples, the mixture samples each indicating a measurement value measured in a mixture of a biological material without the disease and a biological material with the disease.

9. A machine learning method, comprising:
classifying, by a processor, a plurality of samples into three or more clusters according to a feature amount of each of the plurality of samples, the plurality of samples each including the feature amount and a label indicating one of a first value and a second value;
combining, by the processor, some clusters among the three or more clusters to form a combined cluster, based on information on a number of samples with labels indicating the first value among the plurality of samples;
calculating, by the processor, an accuracy level of each of the plurality of samples with respect to the first value or the second value, based on a result of classifying the plurality of samples into the combined cluster and one or more remaining clusters after the combining among the three or more clusters; and
performing, by the processor, machine learning using samples with accuracy levels not meeting a prescribed condition more preferentially than samples with accuracy levels meeting the prescribed condition among the plurality of samples.

10. A machine learning apparatus, comprising:
a memory configured to store therein a plurality of samples each including a feature amount and a label indicating one of a first value and a second value; and
a processor configured to
classify the plurality of samples into three or more clusters according to the feature amount of each of the plurality of samples,
combine some clusters among the three or more clusters to form a combined cluster, based on information on a number of samples with labels indicating the first value among the plurality of samples,
calculate an accuracy level of each of the plurality of samples with respect to the first value or the second value, based on a result of classifying the plurality of samples into the combined cluster and one or more remaining clusters after combining among the three or more clusters, and
perform machine learning using samples with accuracy levels not meeting a prescribed condition more preferentially than samples with accuracy levels meeting the prescribed condition among the plurality of samples.

* * * * *